United States Patent
Pan et al.

(10) Patent No.: US 11,414,624 B2
(45) Date of Patent: Aug. 16, 2022

(54) RANDOM INTRAESTERIFICATION

(71) Applicant: Advanta Holdings BV, Breda (NL)

(72) Inventors: Lucas Guillermo Pan, Mar del Plata (AR); Eduardo Pedro Dubinsky, Buenos Aires (AR); Martin Oscar Grondona, Mar del Plata (AR); Andrés Daniel Zambelli, Mar del Plata (AR); Alberto Javier Leon, Mar del Plata (AR)

(73) Assignee: Advanta Holdings BV, Breda (NL)

( * ) Notice: Subject to any disclaimer, the term of this patent is extended or adjusted under 35 U.S.C. 154(b) by 0 days.

(21) Appl. No.: 14/414,692

(22) PCT Filed: Jul. 22, 2013

(86) PCT No.: PCT/EP2013/065408
§ 371 (c)(1),
(2) Date: Jan. 13, 2015

(87) PCT Pub. No.: WO2014/016245
PCT Pub. Date: Jan. 30, 2014

(65) Prior Publication Data
US 2015/0166932 A1    Jun. 18, 2015

(30) Foreign Application Priority Data

Jul. 24, 2012  (WO) ............. PCT/EP2012/064546

(51) Int. Cl.
*C11C 3/10*  (2006.01)
*A23D 9/00*  (2006.01)
*C12P 7/6472*  (2022.01)

(52) U.S. Cl.
CPC .......... *C11C 3/10* (2013.01); *A23D 9/00* (2013.01); *C12P 7/6472* (2013.01)

(58) Field of Classification Search
CPC ........ C11C 3/10; C12P 7/6472; C12P 7/6454; A23D 9/00
(Continued)

(56) References Cited

U.S. PATENT DOCUMENTS 4,275,081 A * 6/1981 Coleman et al. ............... 426/33
6,277,433 B1   8/2001 Lantz et al.
(Continued)

FOREIGN PATENT DOCUMENTS

ES   WO 2008006597 A2 * 1/2008 ............... A23D 7/02
RU      2303363 C2      7/2007
WO      2006133124 A1  12/2006

OTHER PUBLICATIONS

H.H. Hustedt, Interesterification of edible oils, Jun. 1976, Journal of the American Oil Chemists' Society, vol. 53, Issue 6, pp. 390-392. (Year: 1976).*

(Continued)

*Primary Examiner* — Emily M Le
*Assistant Examiner* — Tynesha L McClain
(74) *Attorney, Agent, or Firm* — Rudy J. Ng; Bret E. Field; Bozicevic, Field & Francis LLP

(57) ABSTRACT

The present invention relates to a method for modifying one or more types of triglycerides in a fat, comprising subjecting a single fat selected from the group consisting of high stearic high oleic sunflower oil, high stearic high oleic soybean oil, high stearic high oleic rapeseed oil, high stearic high oleic cottonseed oil, palm olein and shea olein to an intraesterification process in which the fatty acids of the triglycerides of said oil or fat are randomly redistributed between the triglycerides to obtain an oil or fat with a modified solid fat content (SFC) profile. Further, the present invention relates to the obtained fats and use thereof.

18 Claims, 2 Drawing Sheets

Let A,B,C, etc, the molar percentages of fatty acids a,b,c,etc

Glyceride aaa = 1 x AxAxA/10000 mole %

Glyceride aab = 3 x AxAxB/10000 mole %

Glyceride abc = 3 x AxBxC/10000 mole %

If in the original oil SUU>>SUS by means of randomization part of SUU will switch to SUS/SSU i.e.  S=       25 %
      U=       75 %

SUS+SSU   14,1 %
      SUU+USU   42,2 %
      SSS        1,6 %
      UUU       42,2 %
      Total    100,0 %

(58) Field of Classification Search
USPC .......................................................... 426/601
See application file for complete search history.

(56) References Cited

U.S. PATENT DOCUMENTS

2003/0161934 A1* 8/2003 Floter ...................... A23D 9/00
426/601
2011/0039008 A1* 2/2011 Oonishi ................. A23D 7/003
426/585

OTHER PUBLICATIONS

Lien, Eric L. "The role of fatty acid composition and positional distribution in fat absorption in infants", The Journal of Pediatrics, vol. 125, No. 5, Part 2, Nov. 1994, pp. S62-S68.
Neff et al. "Oxidative Stability of Natural and Randomized High-Palmitic- and High-Stearic-Acid Oils from Genetically Modified Soybean Varieties", Journal of the American Oil Chemists' Society (JAOCS), vol. 76, No. 7, 1999, pp. 825-831.

* cited by examiner

Fig. 1

Let A,B,C, etc, the molar percentages of fatty acids a,b,c,etc

Glyceride aaa = 1 x AxAxA/10000 mole %

Glyceride aab = 3 x AxAxB/10000 mole %

Glyceride abc = 3 x AxBxC/10000 mole %

If in the original oil SUU>>SUS by means of randomization part of SUU will switch to SUS/SSU

| i.e. | | |
|---|---|---|
| | S= | 25 % |
| | U= | 75 % |
| | SUS+SSU | 14,1 % |
| | SUU+USU | 42,2 % |
| | SSS | 1,6 % |
| | UUU | 42,2 % |
| | Total | 100,0 % |

Fig. 2

| Temp. (°C) | HSHO | HSHO Olein | HSHO Randomized | Olein Randomized | HSHO Random. (2nd trial) |
|---|---|---|---|---|---|
| 0 | 39.9 | 37.5 | 29.1 | 27.5 | 31.3 |
| 5 | 30.2 | 28.8 | 27 | 21.4 | 24.7 |
| 10 | 20 | 15.3 | 16.7 | 14.2 | 18.2 |
| 15 | 6.1 | 3 | 9.4 | 7.8 | 10.7 |
| 20 | 3.6 | 2.8 | 3.7 | 0.7 | 2.1 |
| 25 | 4.3 | 2.2 | 3.7 | 2.8 | 2.3 |

RANDOM INTRAESTERIFICATION

The present invention relates to the process of intraesterification of fats. In this process one or more types of triglycerides are modified by redistribution of the fatty acids between the triglycerides.

Some food products, such as margarine, spreads, coatings, fillings, and cooking oils, require specific properties such as spreadability, firmness, plasticity, mouthfeel and the release of flavour. Natural vegetable fats or oils used for food products often do not have these properties and require modification before they can be used. The main processes used for modification of fats or oils are fractionation, hydrogenation, and intraesterification. These processes are known in the art and are, for instance, described in "Food Fats and Oils", Ninth Edition; Institute of Shortening and Edible Oils.

Fractionation is the process in which the liquid and solid constituents of a fat or oil are separated and relies on the differences in melting points. Hydrogenation is a chemical reaction commonly used to convert unsaturated fatty acids to saturated fatty acids. Apart from converting liquid oils to semi-solids and/or solids, hydrogenation also increases the oxidative and thermal stability of the fat or oil. Hydrogenation can be partial or complete. Partial hydrogenation results in oils and soft solid fats and is often used in the production of cooking oils and margarines. A major disadvantage of partial hydrogenation is that it results in high levels of trans-isomers which have been implicated in cardiovascular disease.

In intraesterification two or more desired oils or fats are blended and the fatty acids are redistributed between the triglycerides of these oils or fats. The selection and proportions of oil or fat types for in the reaction mixture determines the properties of the resulting oil or fat. Intraesterification can be performed by chemical or enzymatic processes. In chemical intraesterification two or more desired oils are blended, dried and a catalyst such as sodium methoxide is added. This process results in the random distribution of the fatty acids across the glycerol backbones of the triglycerides. Enzymatic esterification involves the random or position-specific redistribution of fatty acids by using an enzyme.

The present inventors have applied the random redistribution of fatty acids with only one fat type, or one single fat type, instead of two or more fat types. The process in which only one fat type is used is herein referred to as "intraesterification". This process can be applied to relatively new modified oils like high stearic high oleic oils in which a significant amount of saturated-unsaturated-unsaturated (SUU) type triglycerides is present.

It is thus the object of the present invention to modify the solid fat content (SFC) profile of oils. Specifically, it is the object of the present invention to increase the amount of saturated-unsaturated-saturated (SUS) type, saturated-saturated-unsaturated (SSU) type, and saturated-saturated-saturated (SSS) type triglycerides in one fat type or oil The invention thus provides a method for modifying one or more types of triglycerides in a fat or oil, comprising subjecting a single fat or oil selected from the group consisting of high stearic high oleic sunflower oil, high stearic high oleic soybean oil, high stearic high oleic rapeseed oil, high stearic high oleic cottonseed oil, palm olein and shea olein to an intraesterification process in which the fatty acids of the triglycerides of said fat are randomly redistributed between the triglycerides to obtain a fat with a modified solid fat content (SFC) profile and/or to obtain a fat with an increased melting point. The main characteristic in these types of oil is that U (unsaturate fatty acid) is essentially O (oleic acid) and that S (saturate fatty acid) is essentially St (stearic acid). This characteristic differentiates this type of oils from regular oils in which the main U is L (linoleic The differences between both types of SUS Triglycerides are melting behavior and oxidative stability. SOS type (saturate-Oleic-saturate) has melting points above 34° C. This fact confers them very special characteristics depending on their relative concentration in the matrix (commercial fats and oils) in which they are present. When the concentration is high (about 80%), as in cocoa butter, the fat is brittle at room temperature and melts completely in the mouth (body temperature), which are the highly appreciated characteristics of chocolate and cocoa butter alternatives. When the concentration is still significant (about 35%), they can be used as structuring fats i.e. in margarines and spreads. This means the capacity of retaining very high amounts of liquid oils in a special crystal network, that confers these kind of products the spreadability at low temperatures (when taking from the fridge) and a melting stability at room temperature by retaining the liquid oil. This doesn't happen with SLS type of triglycerides. When the randomization happens with high stearic high oleic oils, because of the starting TAG composition, the resulting SUS concentration increases to relative lower levels than those needed for cocoa butter alternatives or structuring fats. Anyway, the change in SFC profile or melting behavior is enough in order to use this randomized fats in margarine, fillings and bakery applications.

Another important characteristic is the oxidative stability. This is because the oxidation rate of linoleic acid (the main one in most of the liquid regular seed oils) is 40 times faster than oleic acid. This means that triglycerides in which U (unsaturated fatty acid) is L (linoleic acid) and accordingly the commercial fats with this kind of triglycerides, has a lower shelf life (or rancidity resistance) than those in which U is O (oleic acid).

A third significant point is when S (saturate fatty acid) is stearic acid and U is oleic acid. (this is valid for high stearic high oleic oils and fractions but not for palm oleins in which the main S is palmitic acid). Stearic acid is the only saturated fatty acid with the ability of generating solid or semisolid fats that is not considered harmful from a nutritional point of view because it has a neutral behavior regarding LDL cholesterol ("bad cholesterol"). On the other hand a high concentration of oleic acid (a stable unsaturated) has a positive effect in lowering LDL cholesterol. In that way the HSHO oils (high stearic high oleic oils) and oleins, are a good alternative to trans fats and other saturates (like palm oil and fractions), that increases de LDL cholesterol and the CVD (cardiovascular disease) risk.

Further, the high stearic high oleic oils and fractions preferably used in the present invention (coming from modified traditional crops like sunflower, rapeseed, soybean, cottonseed) being originated from annual crops are more sustainable than tropical fats, specially because of the clearing of rainforest that takes place in the main palm oil producing countries, with very deleterious effect on environment.

It was found that the solid fat content (SFC) of fats and/or oils can be modified by the process of intraesterification. With this process it is now possible to increase the amount of saturated-unsaturated-saturated (SUS) type, saturated-saturated-unsaturated (SSU) type, and saturated-saturated-saturated (SSS) type triglycerides in one fat type or oil, which is normally rich in saturated-unsaturated-unsaturated (SUU) type triglycerides. Hereby, the functional properties of the one fat type or oil can be improved for food applications, such as, but not limited to, margarines, spreads, shortenings, coatings, fillings, and cooking oils.

The invention resides in applying the randomization process to relatively new oils that yield a special combination of the different kinds of TAG's and that also are a new source with other potential advantages, in particular from a nutritional and sustainability points of view.

Saturated-unsaturated-saturated (SUS) type triglycerides in high stearic high oleic (HSHO) sunflower or high stearic high oleic (HSHO) soybean oils have a higher melting point than SUU type (saturated-unsaturated-unsaturated). The increasing of SUS and the decreasing of SUU composition changes the melting range (or solid fat content) improving the functionality of the fats in which this happens for the applications mentioned above.

The terms "a fat" or "one fat" as used herein is intended to refer to one oil or fat type, or single oil or fat type and not to a combination of different oil or fat types.

Fats consist of a wide group of compounds that are generally soluble in organic solvents and generally insoluble in water. Chemically, fats are triglycerides, triesters of glycerol and any of several fatty acids. In the context of the present invention the term "fat" or "fats" is intended to refer to a mixture of triglycerides. A triglyceride, also referred to as TG, triacylglycerol, TAG, or triacylglyceride, is an ester derived from glycerol and three fatty acids. The fatty acids in a fat can be any fatty acid. A fatty acid is a carboxylic acid with a long aliphatic tail (chain), and is either saturated or unsaturated. Fatty acids that have double bonds are known as unsaturated. Unsaturated fats have a lower melting point and are more likely to be liquid. Fatty acids without double bonds are known as saturated. Saturated fats have a higher melting point and are more likely to be solid. As such, fats may be either solid or liquid at room temperature, depending on its structure and composition. Commonly, liquid fats are called oils. In this application the terms fat and oil can be used interchangeably.

As mentioned above the term "fat" as used herein refers to a mixture of triglycerides. The mixture of triglycerides may comprise one or more types of triglycerides. Types of triglycerides include for instance unsaturated-unsaturated-unsaturated (UUU), saturated-unsaturated-unsaturated (SUU), unsaturated-saturated-unsaturated (USU), unsaturated-unsaturated-saturated (UUS), saturated-saturated-unsaturated (SSU), saturated-unsaturated-saturated (SUS), unsaturated-saturated-saturated (USS), and saturated-saturated-saturated (SSS).

The term "fat" as used herein also refers to "oil", "fat", and "lipid". The words "oil" and "fat" are used interchangeably herein.

The fat type can be obtained from any source. Preferably, the fat is obtained from a vegetable source, including, but not limited to the following seed varieties: HSHO soybean, HSHO rapeseed, HSHO sunflower seed, HSHO cottonseed, palm and shea fruits.

The method of the present invention is particular suitable for fat types which comprise stearic acids and/or oleic acids, such as, but not limited to, high stearic high oleic (HSHO) sunflower oil, high stearic high oleic (HSHO) soybean oil, high stearic high oleic rapeseed oil, and high stearic high oleic (HSHO) cottonseed oil. This process is also suitable for some special palm olein fractions and shea olein.

Advantageously, the solid fat content (SFC) of the present fat type is changed by switching saturated-unsaturated-unsaturated (SUU) type triglycerides into saturated-unsaturated-saturated (SUS) type triglycerides, saturated-saturated-unsaturated (SSU) type triglycerides and/or saturated-saturated-saturated (SSS) type triglycerides Intraesterification as used herein refers to the process in which fatty acids are redistributed between the triglycerides of only one fat type. The process of intraesterifying triglycerides of the present invention is performed by chemical reactions or by enzymatic processes with non specific 1,3 enzymes. Chemical reactions generally involve catalysis by sodium methoxide as described in ("Food Fats and Oils", Ninth Edition; Institute of Shortening and Edible Oils In a preferred embodiment the present randomly redistribution is carried out by a temperature within the range of 60 to 90° C., preferably 75 to 85° C., in the presence of a sodium methoxide catalyst. The present process provides an efficient method for intraesterification, of single fats resulting in a fat with an increased solid fat content (SFC) profile, when compared to the untreated singe fats.

Alternatively, the present randomly redistribution is carried out by enzymatic processes.

The term "between" in the context of the present invention is intended to refer to both "within the triglycerides" and "amongst the triglycerides".

The terms "redistribution" and "exchange" are used interchangeably herein.

The triglyceride composition of the intraesterified product can be predicted by means of statistical equations based on the starting fatty acid composition as is described in the Examples.

It is a further object of the present invention to provide a fat, wherein one or more types of triglycerides of said fat has been modified by intraesterifying the fatty acids to obtain a random redistribution of the fatty acids between the triglycerides. Preferably, the level of saturated-unsaturated-saturated (SUS) type, saturated-saturated-unsaturated (SSU), and/or saturated-saturated-saturated (SSS) type triglycerides in said fat is increased, changed, altered or modified as compared to the level of saturated-unsaturated-saturated (SUS) type, saturated-saturated-unsaturated (SSU), and/or saturated-saturated-saturated (SSS) type triglycerides in a fat that has not been modified.

The fat obtained by the method of the present invention can be used in food applications, including, but not limited to, margarines, spreads, confectionery products and cooking oils.

The fat produced by the method of the present invention can also be used as a third component to decrease the amount of structuring fat used in a blend.

The present invention will be further illustrated in the Examples that follow and that are not intended to limit the invention in any way. Reference is made to the following figures.

FIGURES

FIG. 1 shows a predictive equation for random intraesterification.

FIG. 2 shows the solid fat content of HSHO oils and oleins by NMR before and after the randomization.

EXAMPLES

Example 1

Predictive Equation

A predictive equation has been obtained to indicate the triglycerides' (TAG) composition after the intraesterification process based on the triglycerides (TAG) and fatty acid (FA)

composition of the fat before the intraesterification process. The predictive equation is shown in FIG. 1.

Example 2

Preliminary Trial of Random Intraesterification 100 g of high stearic high oleic HSHO sunflower oil or olein are placed in the randomization reactor with agitation at 78-82° C. 0.5 g of catalyst sodium methoxide are added to the reactor. Randomization time used: 3.5 hrs. The reaction is stopped by the neutralization of the catalyst with powder citric acid. These products are removed by washing 4 times with 150 ml of warm (about 70° C.) distilled water. The product is dried with anhydrous sodium sulphate.
Chromatographic Analysis of TAGs and Fatty Acids The TAG composition of the different stearin fractions was determined by GC using an Agilent 6890 gas chromatograph (Palo Alto, Calif.) equipped with a Quadrex Aluminium-Clad 40065HT (30 m length, 0.25 mm i.d., 0.1 μm film thickness (Woodbridge, Conn., USA) and a flame ionization detector. Hydrogen was used as the carrier gas at a linear rate of 50 cm/s and split ratio 1:80. The injector and detector temperatures were 360 and 370° C. respectively, the oven temperature was 335° C., and a head pressure gradient from 100 to 180 kPa was applied. The relative response of the FID was corrected according to the method of Carelli and Cert 1993 (Comparative study of the determination of triacylglycerols in vegetable oils using chromatographic techniques. *J. Chromatogr.* 630, 213-222).

Fatty acids were analyzed as their methyl esters in a similar chromatograph but equipped with a Supelco SP-2380 fused silica capillary column (30 m length; 0.25 mm i.d.; 0.20 μm film thickness: Bellefonte, Pa.). The analysis conditions were carrier gas (hydrogen) flow at 28 cm·s−1, detector and injector temperature were 200° C., whereas oven temperature was kept at 170° C.

Methylation of the TAG fatty acids was carried out at 80° C. for 1 h after adding a volume of 1.5 mL of methanol/toluene/sulphuric acid (88/10/2; v/v/v) to 5 mg of fat.

For both samples (oil and olein) there are significant increments (about 30 and 60% respectively) in the SUS content by decreasing the SUU content. The increment in SUS yields a better behavior in some applications by an increasing of the solid fat content (SFC) at 15° C. The impact of decreasing SUU, involves a reduction in the solid fat content (SFC) at fridge temperature (below 10° C.)

Example 3

Second and Third Trial of Random Intraesterification

Two more trials were performed as described in Example 2, specifically one additional trial for the olein and 2 additional trials for the oil).

The results of trials 1, 2 and 3 are shown in Table 1 below.

TABLE 1

| Oil type | TAG type | | | |
|---|---|---|---|---|
| | SUS | SUU | UUU | SSS |
| HSHO oil | 9.4 | 51.8 | 38.8 | 0.0 |
| Predicted for oil | 12.7 | 41.3 | 44.7 | 1.3 |
| HSHO oil randomized 1 | 12.4 | 39.8 | 47.8 | n.d. |
| HSHO oil randomized 2 | 12.0 | 40.5 | 46.9 | 0.6 |
| HSHO oil randomized 3 | 12.0 | 40.5 | 46.7 | 0.8 |
| HSHO Olein | 7.0 | 51.9 | 41.1 | 0.0 |
| Predicted for olein | 11.3 | 40.1 | 47.5 | 1.1 |

TABLE 1-continued

| Oil type | TAG type | | | |
|---|---|---|---|---|
| | SUS | SUU | UUU | SSS |
| HSHO olein randomized 1 | 11.5 | 40.2 | 48.4 | n.d. |
| HSHO olein randomized 2 | 11.6 | 40.1 | 47.6 | 0.7 | n.d. = not detected
1 is preliminary trial of example 2
2 and 3 are new trials of example 3

It follows that in both the oil and the olein the SUU content is significantly decreased and the SUS content is significantly increased by performing the random intraesterification of the invention.

Example 4

Determination of Solid Fat Content

The solid fat content (SFC) of the HSHO oil, HSHO olein fraction and the intraesterified products of examples 2 and 3 were determined using NMR. (Nuclear magnetic resonance)

FIG. 2 shows that the solid fat content of the random intraesterified products of example 2 and 3 is modified compared with the solid fat content of the original HSHO oil and HSHO olein fraction, becoming suitable to be used in some confectionery fillings and as part of the fat phase of margarines and spreads.

Example 5

Determination of Melting Point

The melting point of the HSHO oil, HSHO olein fraction and random intraesterified products of examples 2 and 3 was determined using standard techniques.

Table 2 shows that the melting point of the random intraesterified HSHO oil and HSHO olein fraction are significantly increased when compared to the original HSHO oil and HSHO olein fraction.

TABLE 2

| Sample | Melting point (° C.) |
|---|---|
| HSHO | 14.3 |
| HSHO olein | 12.1 |
| HSHO intraesterified | 27.2 |
| HSHO olein intraesterified | 24.8 |

The invention claimed is:

1. A method for modifying one or more types of triglycerides in a single fat type, comprising subjecting a single oil or fat type selected from the group consisting of high stearic high oleic sunflower oil, high stearic high oleic soybean oil or olein fraction, high stearic high oleic rapeseed oil or olein fraction, and high stearic high oleic cottonseed oil or olein fraction, to an intraesterification process in which the fatty acids of the triglycerides constituting said single oil or fat type are randomly redistributed within said triglycerides and/or amongst said triglycerides of only said single oil or fat type to obtain an oil or fat with a modified solid fat content (SFC) profile.

2. The method according to claim 1, wherein the random redistribution is carried out by a temperature within the range of 60 to 90° C., in the presence of a sodium methoxide catalyst.

3. The method according to claim 1, wherein the random redistribution is carried out by an enzymatic process.

4. A composition comprising a triglyceride or fat obtainable by a method comprising subjecting a single oil or fat type selected from the group consisting of high stearic high oleic sunflower oil, high stearic high oleic soybean oil or olein fraction, high stearic high oleic rapeseed oil or olein fraction, and high stearic high oleic cottonseed oil or olein fraction, to an intraesterification process in which the fatty acids of the triglycerides constituting said oil or fat are randomly redistributed within said triglycerides and/or amongst said triglycerides of only said single oil or fat type to obtain an oil or fat with a modified solid fat content (SFC) profile.

5. The composition as claimed in claim 4, wherein the composition is a food.

6. The composition as claimed in claim 5, wherein the food is selected from the group consisting of margarines, spreads, coatings, fillings, confectionery products and cooking oils.

7. The method according to claim 1, wherein the method increases an amount of saturated-unsaturated-saturated (SUS) triglycerides, saturated-saturated-unsaturated (SSU), and/or saturated-saturated-saturated (SSS) triglycerides in the oil or fat.

8. The method according to claim 1, wherein the method increases the solid fat content (SFC) profile of the oil or fat.

9. The method according to claim 1, wherein the intraesterification process comprises contacting said single oil or fat type with a catalyst.

10. The method according to claim 1, wherein the intraesterification process comprises contacting said single oil or fat type with an enzyme.

11. The method according to claim 10, wherein the enzyme is a non-specific 1,3 enzyme.

12. A method for modifying one or more types of triglycerides in a single fat type, comprising subjecting a single oil or fat type selected from the group consisting of high stearic high oleic sunflower oil, high stearic high oleic soybean oil or olein fraction, high stearic high oleic rapeseed oil or olein fraction, and high stearic high oleic cottonseed oil or olein fraction, to an intraesterification process in which the fatty acids of the triglycerides of said single oil or fat type are randomly redistributed within said triglycerides and/or amongst said triglycerides of only said single oil or fat type to obtain an oil or fat with a modified solid fat content (SFC) profile, wherein the random redistribution is carried out at temperature within the range of 60 to 90° C. in the presence of a catalyst or by an enzymatic process.

13. The method according to claim 12, wherein the method increases an amount of saturated-unsaturated-saturated (SUS) triglycerides, saturated-saturated-unsaturated (SSU), and/or saturated-saturated-saturated (SSS) triglycerides in the oil or fat.

14. The method according to claim 13, wherein the method increases the solid fat content (SFC) profile of the oil or fat.

15. The method according to claim 14, wherein the random redistribution is carried out at temperature within the range of 60 to 90° C., in the presence of a catalyst.

16. The method according to claim 15, wherein the catalyst is a sodium methoxide catalyst.

17. The method according to claim 14, wherein the random redistribution is carried out by an enzymatic process.

18. The method according to claim 17, wherein the enzyme is a non-specific 1,3 enzyme.

* * * * *